United States Patent
Sang et al.

(10) Patent No.: US 10,494,324 B2
(45) Date of Patent: Dec. 3, 2019

(54) PROCESS FOR PD-CATALYZED HYDROXYCARBONYLATION OF DIISOBUTENE: EFFECT OF SOLVENT

(71) Applicant: EVONIK DEGUSSA GMBH, Essen (DE)

(72) Inventors: Rui Sang, Liaocheng (CN); Peter Kucmierczyk, Herne (DE); Kaiwu Dong, Bo Zhou (CN); Ralf Jackstell, Rostock (DE); Matthias Beller, Ostseebad Nienhagen (DE); Robert Franke, Marl (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 16/216,004

(22) Filed: Dec. 11, 2018

(65) Prior Publication Data

US 2019/0194111 A1      Jun. 27, 2019

(30) Foreign Application Priority Data

Dec. 21, 2017   (EP) .................................... 17209307

(51) Int. Cl.
| | | |
|---|---|---|
| *C07C 51/14* | (2006.01) | |
| *C07C 53/00* | (2006.01) | |
| *B01J 31/00* | (2006.01) | |
| *B01J 31/22* | (2006.01) | |
| *B01J 31/24* | (2006.01) | |
| *B01J 31/30* | (2006.01) | |
| *C07C 53/128* | (2006.01) | |

(52) U.S. Cl.
CPC ........... *C07C 51/14* (2013.01); *B01J 31/2234* (2013.01); *B01J 31/2295* (2013.01); *B01J 31/2409* (2013.01); *B01J 31/30* (2013.01); *B01J 2231/321* (2013.01); *B01J 2531/842* (2013.01); *C07C 53/128* (2013.01)

(58) Field of Classification Search
CPC .. C07C 51/14; C07C 53/128; B01J 2231/321; B01J 31/2234; B01J 31/2295
See application file for complete search history.

(56) References Cited

U.S. PATENT DOCUMENTS

| | | |
|---|---|---|
| 3,641,074 A | 2/1972 | Fenton |
| 3,968,133 A | 7/1976 | Knifton |

FOREIGN PATENT DOCUMENTS

| | | |
|---|---|---|
| DE | 887644 C | 8/1953 |
| GB | 1595037 A | 8/1981 |
| WO | 2014/005854 A1 | 1/2014 |

OTHER PUBLICATIONS

U.S. Appl. No. 16/188,995, filed Nov. 13, 2018, Sang et al.
U.S. Appl. No. 16/189,029, filed Nov. 13, 2018, Sang et al.
U.S. Appl. No. 16/215,991, filed Dec. 11, 2018, Sang et al.
U.S. Appl. No. 16/216,020, filed Dec. 11, 2018, Sang et al.
U.S. Appl. No. 16/216,037, filed Dec. 11, 2018, Sang et al.
U.S. Appl. No. 16/216,053, filed Dec. 11, 2018, Sang et al.
European Search Report dated Jun. 21, 2018 in EP 17 20 9307 (5 pages).

*Primary Examiner* — Sikarl A Witherspoon
(74) *Attorney, Agent, or Firm* — Smith, Gambrell & Russell, LLP

(57) ABSTRACT

A process for Pd-catalyzed hydroxycarbonylation of diisobutene in an acetic acid solvent in the presence of a ligand having the following structure:

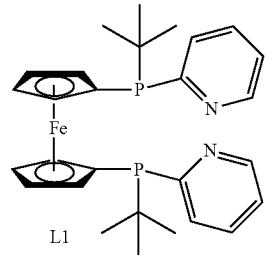

In contrast to reaction solvents such as formic acid or 3,5,5 hexanoic acid the conversion rates were improved and greater than 90% at a reaction temperature of 120° C. and CO pressure of 40 bar.

5 Claims, No Drawings

PROCESS FOR PD-CATALYZED HYDROXYCARBONYLATION OF DIISOBUTENE: EFFECT OF SOLVENT

The invention relates to a process for Pd-catalyzed hydroxycarbonylation diisobutene: Effect of solvent Carboxylic acids including propionic acid, adipic acid and fatty acids are used in the preparation of polymers, pharmaceuticals, solvents and food additives. The routes leading to carboxylic acids generally include the oxidation of hydrocarbons, alcohols or aldehydes, the oxidative cleavage of olefins by ozonolysis, the hydrolysis of triglycerides, nitriles, esters or amides, the carboxylation of Grignard or organolithium reagents, and the halogenation and subsequent hydrolysis of methyl ketones in the haloform reaction.

The hydrocarboxylation of olefins is a highly promising and environmentally-friendly method for obtaining carboxylic acids. Acetic acid is produced by carbonylation of methanol, which is carried out with iodide. In the Koch reaction, the addition of water and carbon monoxide to alkenes is catalyzed by strong bases. This method is effective with alkenes that form secondary and tertiary carbocations, e.g. isobutylene to pivalic acid. The hydrocarboxylation occurring with the simultaneous addition of CO and $H_2O$ to alkenes/alkynes provides a direct and convenient method for synthesizing carboxylic acids.

The object of the invention was to provide a process affording good conversion in the Pd-catalyzed hydroxycarbonylation of diisobutene (DIBN). This reaction should be carried out in one step.

The object is achieved by a process according to Claim 1.
Process comprising the process steps of:
a) addition of diisobutene,
b) addition of a compound comprising Pd, wherein the Pd is capable of forming a complex,
c) addition of the ligand L1:

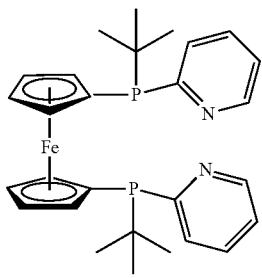

L1 d) addition of acetic acid,
e) feeding in CO,
f) heating the reaction mixture such that the diisobutene is converted to the compound P1:

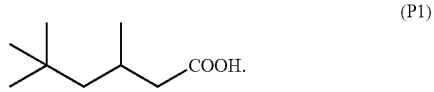

(P1)

In one variant of the process, the compound in process step b) is selected from: $PdCl_2$, $PdBr_2$, $Pd(acac)_2$, $Pd(dba)_2$ (dba=dibenzylideneacetone), $PdCl_2(CH_3CN)_2$.

In one variant of the process, the compound in process step b) is $Pd(acac)_2$.

In one variant of the process, the process comprises the additional reaction step g):

g) addition of p-toluenesulfonic acid (PTSA).

In one variant of the process, the reaction mixture is heated to a temperature in the range from 80° C. to 160° C. in process step f), preferably to a temperature in the range from 100° C. to 140° C.

In one variant of the process, the CO is fed in in process step e) such that the reaction proceeds under a CO pressure in the range from 20 bar to 60 bar, preferably in the range from 30 bar to 50 bar.

The invention is elucidated in more detail by means of a working example below.

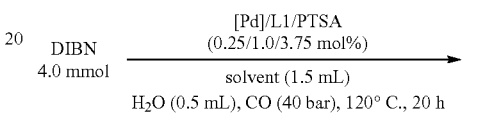

DIBN
4.0 mmol

[Pd]/L1/PTSA
(0.25/1.0/3.75 mol%)

solvent (1.5 mL)
$H_2O$ (0.5 mL), CO (40 bar), 120° C., 20 h

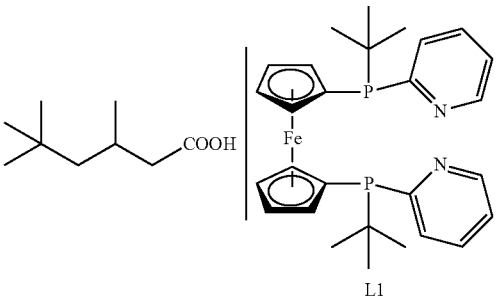

L1

A 4 ml vial was charged with $[Pd(acac)_2]$ (3.05 mg, 0.25 mol %), L1 (20.64 mg, 1.0 mol %), PTSA*$H_2O$ (28.5 mg, 3.75 mol %) and an oven-dried stirrer bar. The vial was then sealed with septa (PTFE-coated styrene-butadiene rubber) and a phenol resin cap. The vial was evacuated and refilled with argon three times. $H_2O$ (0.5 ml), acetic acid (1.5 ml) and diisobutene (DIBN) (4.0 mmol) were added to the vial with a syringe. The vial was placed in an alloy plate, which was transferred to an autoclave (300 ml) of the 4560 series from Parr Instruments under argon atmosphere. After flushing the autoclave three times with CO, the pressure of CO was increased to 40 bar at room temperature. The reaction was conducted at 120° C. for 20 h. On conclusion of the reaction, the autoclave was cooled down to room temperature and cautiously decompressed. Isooctane (100 μl) was then added as internal standard. Conversion was measured by GC analysis.

The experiment described above was repeated with variation of the solvent. All other parameters were maintained.

The results are compiled in the following table.

| Entry | Solvent | Conversion (%) |
|---|---|---|
| 1 | 3,5,5-trimethylhexanoic acid | 88 |
| 2 | Formic acid | 48 |
| 3* | Acetic acid | >99 |

*inventive process

As the experimental results show, the object is achieved by the inventive process.

The invention claimed is:
1. A process comprising:
a) adding diisobutene, forming a reaction mixture,
b) adding of a compound comprising Pd, wherein the Pd is capable of forming a complex,
c) adding the ligand L1:

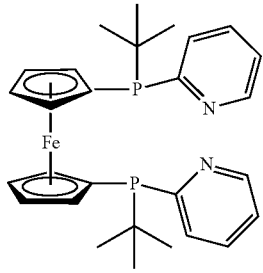

d) adding acetic acid, as a solvent for the reaction mixture,
e) feeding in CO,
f) heating the reaction mixture such that the diisobutene is converted to the compound P1:

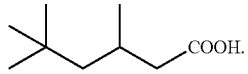

2. The process according to claim 1, wherein the compound in step b) is $PdCl_2$, $PdBr_2$, $Pd(acac)_2$, $Pd(dba)_2$ (dba=dibenzylideneacetone) or $PdCl_2(CH_3CN)_2$.

3. The process according to claim 1, further comprises g) adding p-toluenesulfonic acid.

4. The process according to claim 1, wherein the reaction mixture is heated to a temperature in the range from 80° C. to 160° C. in process step f).

5. The process according to claim 1, wherein the CO is fed in in process step e) such that the reaction proceeds under a CO pressure in the range from 20 bar to 60 bar.

* * * * *